United States Patent
Protopsaltis et al.

(10) Patent No.: US 10,278,741 B2
(45) Date of Patent: *May 7, 2019

(54) TRANSLATING POLYAXIAL SCREW

(71) Applicant: SPINE WAVE, INC., Shelton, CT (US)

(72) Inventors: Dimitri Protopsaltis, Memphis, TN (US); Troy D. Drewry, Memphis, TN (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/989,309

(22) Filed: May 25, 2018

(65) Prior Publication Data

US 2018/0271563 A1    Sep. 27, 2018

Related U.S. Application Data

(63) Continuation of application No. 14/496,557, filed on Sep. 25, 2014, now Pat. No. 9,987,047.

(Continued)

(51) Int. Cl.
*A61B 17/70* (2006.01)

(52) U.S. Cl.
CPC ...... *A61B 17/7041* (2013.01); *A61B 17/7035* (2013.01); *A61B 17/7038* (2013.01)

(58) Field of Classification Search
CPC ............ A61B 17/7035; A61B 17/7038; A61B 17/7041; A61B 17/7001; A61B 17/7032;
(Continued)

(56) References Cited

U.S. PATENT DOCUMENTS 4,887,596 A   12/1989   Sherman
5,002,542 A    3/1991   Frigg
(Continued)

FOREIGN PATENT DOCUMENTS

DE    20213572    12/2002
FR     2789293     8/2000
(Continued)

OTHER PUBLICATIONS

International Search Report for PCT/US18/53065, dated Oct. 29, 2018.
Written Opinion for PCT/US18/53065, dated Oct. 29, 2018.

*Primary Examiner* — Zade Coley
*Assistant Examiner* — Jessica Weiss
(74) *Attorney, Agent, or Firm* — Hoffmann & Baron, LLP (57) ABSTRACT

A translating polyaxial bone anchor for anchoring a connecting rod to a spinal vertebra comprises a fastener having a bone engaging portion and a head, the head defining a socket. An insert is captively retained in the socket and configured for swiveling polyaxial movement therein. The insert includes an elongate connecting element defining an axis, the connecting element projecting outwardly from and through the socket. A yoke having at one end a rod receiving channel for receiving a connecting rod is coupled to the fastener by a coupling member. The coupling member couples the yoke to the insert connecting element for joint polyaxial movement relative to the fastener and for translational movement of the yoke in a direction transverse to the axis of the connecting member. A fastening element is supported by the yoke for securing the connecting rod between the fastening element and the coupling member.

8 Claims, 7 Drawing Sheets

Related U.S. Application Data (60) Provisional application No. 61/887,631, filed on Oct. 7, 2013.

(58) Field of Classification Search
CPC ............. A61B 17/704; A61B 17/7046; A61B 17/8605; A61C 8/00; A61C 8/0048; A61C 8/005; A61C 8/0053; A61C 8/006; A61C 8/0066; A61C 8/0075; A61C 8/0078; A61C 8/0093; A61C 2008/0084
USPC .................................. 606/264–279, 300–321
See application file for complete search history.

(56) References Cited

U.S. PATENT DOCUMENTS

| | | |
|---|---|---|
| 5,129,900 A | 7/1992 | Asher et al. |
| 5,306,275 A | 4/1994 | Bryan |
| 5,312,404 A | 5/1994 | Asher et al. |
| 5,360,431 A | 11/1994 | Puno et al. |
| 5,499,983 A | 3/1996 | Hughes |
| 5,591,166 A | 1/1997 | Bernhardt et al. |
| 5,733,286 A | 3/1998 | Errico et al. |
| 5,735,851 A | 4/1998 | Errico et al. |
| 5,741,255 A | 4/1998 | Krag et al. |
| 5,984,924 A | 11/1999 | Asher et al. |
| 5,997,539 A | 12/1999 | Errico et al. |
| 6,086,588 A | 7/2000 | Ameil et al. |
| 6,110,172 A | 8/2000 | Jackson |
| 6,302,888 B1 | 10/2001 | Mellinger et al. |
| 6,315,779 B1 | 11/2001 | Morrison et al. |
| 6,413,257 B1 | 7/2002 | Lin |
| 6,478,798 B1 | 11/2002 | Howland |
| 6,623,485 B2 | 9/2003 | Doubler et al. |
| 6,755,830 B2 | 6/2004 | Minfelde et al. |
| RE39,035 E | 3/2006 | Finn et al. |
| 7,163,538 B2 | 1/2007 | Altarac et al. |
| 7,306,602 B2 | 12/2007 | Bono et al. |
| 7,335,201 B2 * | 2/2008 | Doubler .............. A61B 17/7035 606/264 |
| 7,338,491 B2 | 3/2008 | Baker et al. |
| 7,635,380 B2 | 12/2009 | Zucherman et al. |
| 7,704,270 B2 | 4/2010 | De Coninck |
| 7,780,706 B2 | 8/2010 | Marino et al. |
| 7,811,310 B2 | 10/2010 | Baker et al. |
| 7,819,902 B2 | 10/2010 | Abdelgany |
| 7,850,718 B2 | 12/2010 | Bette et al. |
| 7,892,257 B2 | 2/2011 | Abdelgany |
| 7,927,359 B2 | 4/2011 | Trautwein |
| 7,955,358 B2 | 6/2011 | Albert |
| 8,012,183 B2 | 9/2011 | Alain |
| 8,044,272 B2 | 10/2011 | Burdett et al. |
| 8,162,990 B2 | 4/2012 | Potash et al. |
| 8,449,578 B2 | 5/2013 | Keiser et al. |
| 8,506,567 B2 | 8/2013 | Ziemek et al. |
| 8,672,979 B2 | 3/2014 | Bishop |
| 9,044,272 B2 | 6/2015 | Shaffrey et al. |
| 9,113,960 B2 * | 8/2015 | Hansell .............. A61B 17/7035 |
| 9,308,027 B2 | 4/2016 | Jackson |
| RE46,115 E | 8/2016 | Albert |
| 9,498,255 B2 | 11/2016 | Lovell et al. |
| 9,750,541 B2 | 9/2017 | Hansell |
| 9,763,701 B2 | 9/2017 | Shaffrey et al. |
| 2002/0022842 A1 | 2/2002 | Horvath et al. |
| 2003/0149432 A1 | 8/2003 | Frigg et al. |
| 2004/0102781 A1 | 5/2004 | Jeon |
| 2004/0177847 A1 | 9/2004 | Foley et al. |
| 2004/0210216 A1 | 10/2004 | Farris et al. |
| 2005/0080420 A1 | 4/2005 | Farris et al. |
| 2005/0154391 A1 | 7/2005 | Doherty et al. |
| 2005/0234451 A1 | 10/2005 | Markworth |
| 2006/0264933 A1 | 11/2006 | Baker et al. |
| 2007/0093819 A1 | 4/2007 | Albert |
| 2007/0274800 A1 | 11/2007 | Mikkonen et al. |
| 2008/0108992 A1 | 5/2008 | Barry et al. |
| 2008/0195159 A1 | 8/2008 | Kloss et al. |
| 2008/0262548 A1 | 10/2008 | Lange et al. |
| 2008/0287994 A1 | 11/2008 | Perez-Cruet et al. |
| 2009/0036929 A1 | 2/2009 | Reglos et al. |
| 2009/0062861 A1 | 3/2009 | Frasier et al. |
| 2009/0182384 A1 | 7/2009 | Wilcox et al. |
| 2009/0210015 A1 | 8/2009 | Cermak et al. |
| 2010/0036417 A1 | 2/2010 | James |
| 2010/0204735 A1 | 8/2010 | Gephart et al. |
| 2010/0241170 A1 | 9/2010 | Cammisa et al. |
| 2011/0301649 A1 | 12/2011 | Hansell |
| 2012/0016425 A1 * | 1/2012 | Shaffrey ............. A61B 17/7032 606/305 |
| 2012/0277805 A1 | 11/2012 | Farris |
| 2012/0283787 A1 * | 11/2012 | Yuan .................. A61B 17/7001 606/305 |
| 2015/0100096 A1 | 4/2015 | Protopsaltis et al. |
| 2015/0223846 A1 | 8/2015 | Shaffrey et al. |
| 2017/0367739 A1 | 12/2017 | Shaffrey et al. |

FOREIGN PATENT DOCUMENTS

| | | |
|---|---|---|
| WO | 1991/05516 | 3/1991 |
| WO | 2002/22030 | 3/2002 |
| WO | 2003/075811 | 9/2003 |
| WO | 2006/102605 | 9/2006 |
| WO | 2008/042948 | 4/2008 |
| WO | 2011056707 A2 | 5/2011 |

* cited by examiner

TRANSLATING POLYAXIAL SCREW

CROSS-REFERENCE TO RELATED APPLICATION

This is a continuation application of U.S. application Ser. No. 14/496,557, filed Sep. 25, 2014, now U.S. Pat. No. 9,987,047, which claims priority to U.S. Provisional Patent Application No. 61/887,631, filed Oct. 7, 2013, the entire contents of which are incorporated by reference herein.

FIELD OF THE INVENTION

The subject invention relates generally to the field of spinal fixation systems and more particularly to an anchor device that incorporates translational and polyaxial fixation to the spine.

BACKGROUND OF THE INVENTION

Several techniques and systems have been developed for correcting and stabilizing injuries to or malformation of the spine. In one type of system, an elongated member such as an elongate bendable rod is disposed longitudinally along a length of the spine, spanning two or more vertebral levels. In certain applications, the rod is bent to correspond to the normal curvature of the spine in the particular region being instrumented, such as the normal kyphotic curvature of the thoracic region or the lordotic curvature of the lumbar region. In accordance with such a system, the rod is engaged to various vertebrae along a length of the spinal column by way of a number of anchor devices that utilize a variety of fixation elements configured to engage specific portions of the vertebra and other bones. For instance, one such fixation element is a hook that is configured to engage the laminae of the vertebra. Another very prevalent fixation element is a bone screw that can be threaded into various parts of the vertebrae, particularly the pedicle.

As these systems have evolved, various degrees of freedom of relative orientation were integrated into the systems in order to accommodate misaligned spinal curvature as well as to minimize rod bending and stress risers in the anchor. Presently, the standard in rod-based spinal systems is a polyaxial pedicle screw which includes a yoke having a slot for receiving a bendable elongate connecting rod that is coupled to a threaded bone engaging shank for polyaxial swiveling movement with respect thereto. One example of such a polyaxial screw is shown and described in commonly assigned U.S. Pat. No. 8,162,990, entitled "Multi-axial Spinal Fixation System", issued on Apr. 24, 2012 to Robert Potash et al. Further advances in the art have now seen anchor systems that include movement of the polyaxial rod-receiving yoke in an additional plane of motion relative to the bone fastener. Such a system is shown, for example, in U.S. Pat. No. 8,449,578, entitled "Multiplanar Bone Anchor System", issued on May 28, 2013 to Matthew L. Kaiser et al.

Nevertheless, improvements in bone anchoring systems that increase the flexibility of accommodating different spine angulations and curvatures as well as minimizing bending of connecting rods and reducing complexity and cost of the anchor are desirable.

SUMMARY OF THE INVENTION

It is an object of the invention to provide an improved polyaxial bone anchor that in a particular aspect comprises a bone screw, collar, ball insert, slider, and yoke. The anchor is assembled so that the polyaxial ball end of the insert is placed into a spherical socket in the top of the bone screw. The spherical socket is then mechanically swaged around the ball end to provide for a threaded stem to assemble the remaining parts of the bone anchor. A slider is then threaded on the stem. The slider is manufactured into a "T" shape that interfaces a "T" slot cut into the bottom of the yoke of the bone anchor. This assembly allows the yoke to translate in the orientation of the slider. The preferred arrangement for this translation is 90 degrees out of phase with the rod slot in the yoke. However, the "T" shaped slider can be assembled in any given angle to provide translation of the yoke in that direction.

DESCRIPTION OF THE EMBODIMENTS

For the purposes of promoting an understanding of the principles of the invention, 1reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
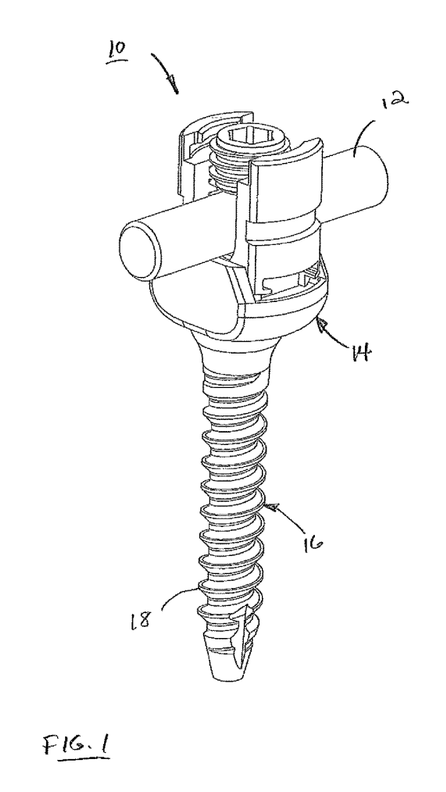
FIG. 1 is a top perspective view of a spinal fixation system utilizing a translating polyaxial anchor device in accordance with an embodiment of the present invention shown in connection with an elongate connecting rod.

The present invention contemplates a spinal fixation system, such as the system 10 depicted in FIG. 1. As is known in the art, the spinal fixation system 10 spans between successive vertebrae of the spine. An elongated member, such as a connecting rod 12, extends along the length of the spine and provides an anchor point for connecting each vertebra to the rod 12. The rod 12, typically formed of stainless steel, is contoured by bending to approximate the normal curvature of the spine for the particular instrumented spinal segments. An anchor device 14 is provided for connecting each of the vertebral segments to the rod 12. These anchor devices 14 may include hooks, bolts, screws or other means for engaging a vertebra. For the purposes of the present arrangement, the anchor device 14 includes a bone engaging fastener 16 which is a bone screw, preferably a pedicle screw. The bone screw 16 includes a threaded elongate shank 18 configured for threaded engagement within a portion of a vertebra, such as the pedicle. More specifically, the anchor device 14 includes features, as will be described that provide for translating and polyaxial connection of the bone screw 16 to rod 12. In a particular example, the shank 18 is configured for engagement within the pedicle of a vertebra of the cervico-thoracic spine. Configurations for use in the lumbar spine and other regions of the spine are also contemplated.

Figure 2:
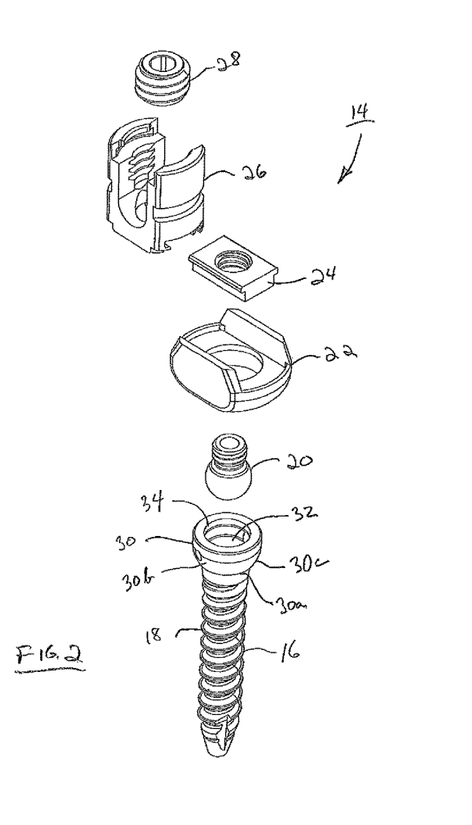
FIG. 2 is a top perspective exploded view of the translating polyaxial anchor device of FIG. 1.

Referring now also to FIG. 2, the elements of the translating polyaxial bone screw 14 are shown in exploded view. Translating polyaxial bone screw 14 comprises bone screw 16, a ball insert 20 configured for captive retention in bone screw 16, a collar 22, a slider 24, a yoke 26 and a fastening element 28. Collar 22 and slider 24 comprise a coupling member for joining yoke 26 to ball insert 20 once ball insert 20 has been captured in bone screw 16, as will be described.

Bone crew 16 further includes a head 30 by which bone screw 16, and ultimately the vertebra, are anchored to the spinal rod 12. In accordance with one arrangement, head 30 defines a spherical socket 32 with a generally circular socket opening 34 facing collar 22. Head 30 includes a lower portion 30*a* for engagement with a surface of the bone, such as the pedicle, and an upper portion 30*b* having a spherical outer surface 30*c*.

Figure 3A:
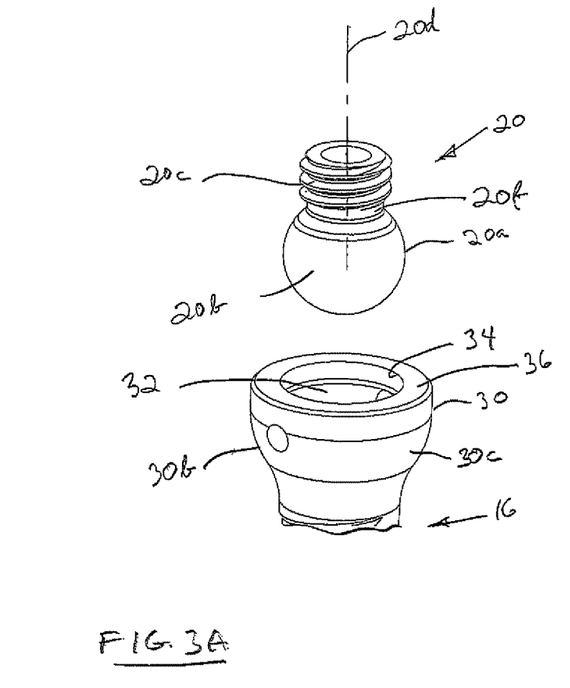
FIGS. 3A and 3B are top perspective views of a sequence of assembling a ball insert to a socket in the fastener of the translating polyaxial anchor device of FIG. 2.
Figure 3B:
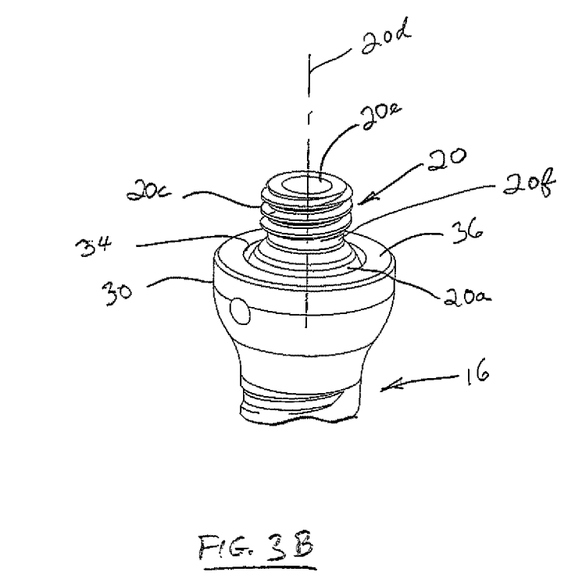

Turning now to the FIGS. 3A and 3B, details of ball insert 20 and the manner in which it is assembled to bone screw 16 are described. Ball insert 20 comprises a first portion 20*a* generally in the form of ball having a spherical outer surface 20*b* and a connecting member 20*c* projecting therefrom. Spherical outer surface 20*b* generally matches but is dimensioned to be slightly less than the dimensions of the spherical inner surface of socket 32. Connecting member 20*c* is generally in the form of an elongate cylindrical stem which defines an axis 20*d* extending along the longitudinal extent. The diameter of cylindrical connecting member 20*c* is less than the diameter of the ball of first portion 20*a*. The outer surface of connecting member 20*c* is preferably threaded. In a preferred arrangement ball insert 20 is formed as a one-piece structure, it being understood that ball insert 20 may also be formed of separate elements that are suitably attached, such as by threading or welding. The upper end of connecting element 20*c* may be formed to have an opening 20*e* particularly configured to receive a tool or other suitable instrument for use in assembling slider 24 thereto, as will be described.

Ball insert 20 is coupled to the bone screw 16 in the following manner. Socket opening 34 is initially formed to have a diameter that is slightly greater than the diameter of the ball of first portion 20*a*. The ball of first portion 20*a* is inserted through opening 34 and into socket 32 of bone screw 16. Once ball 20*a* is received into socket 32, the lip 36 defining opening 34 is swaged or otherwise mechanically crimped to reduce the diameter of opening 34 to a dimension less than the diameter of ball 20*a*, but still greater than the diameter of connecting element 20*c*. As such, ball 20*a* and thereby the ball insert 20 is captively retained in socket 32 of bone screw 16 allowing insert 20 with connecting member 20*c* to swivel in a polyaxial motion relative to bone screw 16. It should be appreciated that ball insert 20 may be captively retained in socket 32 of bone screw 16 by other means, such as by suitable clips or rings.

Figure 4A:
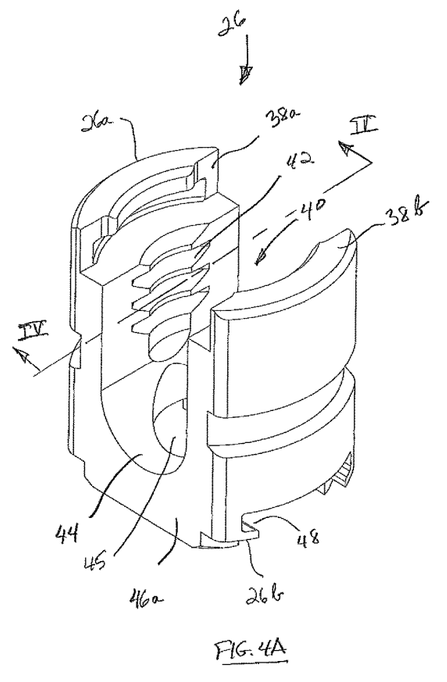
FIG. 4A is a top perspective view of the yoke of the translating polyaxial anchor device of FIG. 2.
Figure 4B:
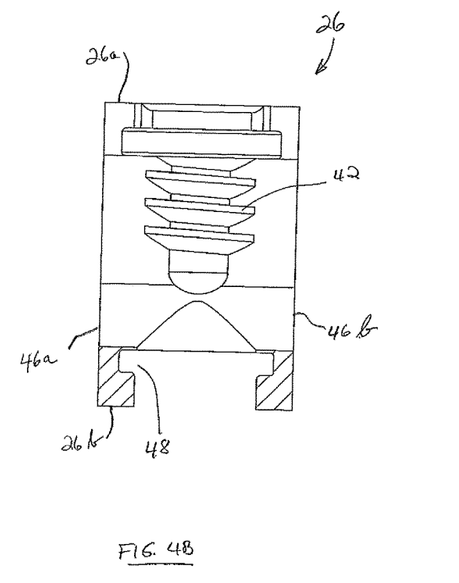
FIG. 4B is a cross-sectional view of the yoke as seen along viewing lines IV-IV of FIG. 4A.
Figure 8:
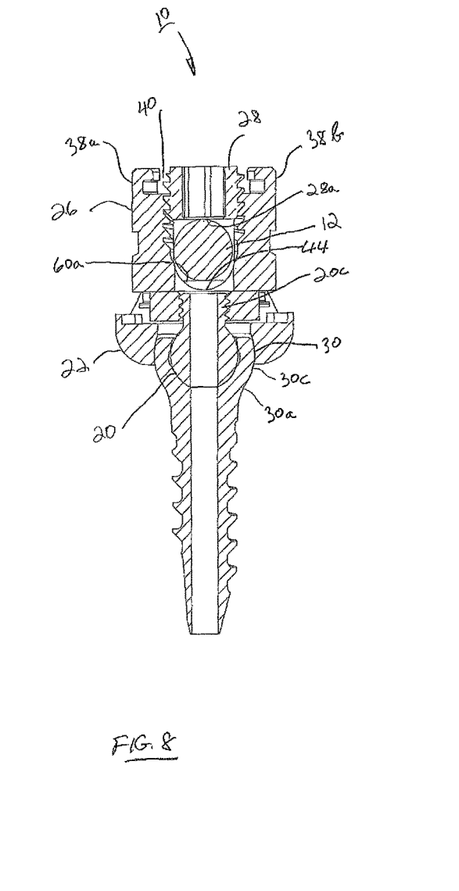
FIG. 8 is a side cross-sectional view of the spinal fixation system of FIG. 1.

Turning now to FIGS. 4A and 4B, details of yoke 26 are described. Yoke 26 is of generally cylindrical configuration having an upper end 26*a* and a lower end 26*b*. Yoke 26 includes a pair of spaced opposing arms 38*a* and 38*b* that define therebetween a yoke channel 40 that extends through upper yoke end 26*a*. The gap between arms 38*a* and 38*b*, and consequently the width of the channel 40, is sized to closely fit spinal rod 12, as best seen in FIG. 8. Yoke 26 includes a surface 44 at the bottom of channel 40, surface 44 extending between and joining yoke arms 38*a* and 38*b*. The bottom surface 44 in one arrangement is formed as a curved surface and has an opening 45 extending therethrough in communication with channel 40. Arms 38*a* and 38*b* define internal threads 42 for engaging fastening element 28, as will be further described. Yoke 26 is truncated on either side of channel 40 by a pair of spaced opposing flat surfaces 46*a* and 46*b* that define external surfaces of arms 38*a* and 38*b*. Flat surfaces 46*a* and 46*b* are substantially parallel to each other and are disposed generally perpendicular to the an formed by channel 40 that extends through flat surfaces 46*a* and 46*b* and that is configured to receive spinal rod 12. It should be appreciated that flat surfaces 46*a* and 46*b* may also be disposed at other transverse angles relative to channel 40 to provide translation of the yoke channel 40 in different angular directions. Flat surfaces 46*a* and 46*b* provide keying surfaces for engagement with cooperative surfaces of collar 22, as will be described.

The opposite end 26*b* of yoke 26 is formed to have a slot 48 in the form of a T-bar configuration. T-bar slot 48 extends through both arms 38*a* and 38*b* fully across lower end 26*b* of yoke 26 and substantially perpendicular to the axis formed by channel 40. T-bar slot 48 is provided to slidably engage with slider 24, as will be described. T-bar 48 may also be disposed at angles other than 90 degrees with respect to the axis of channel 40.

Figure 5A:
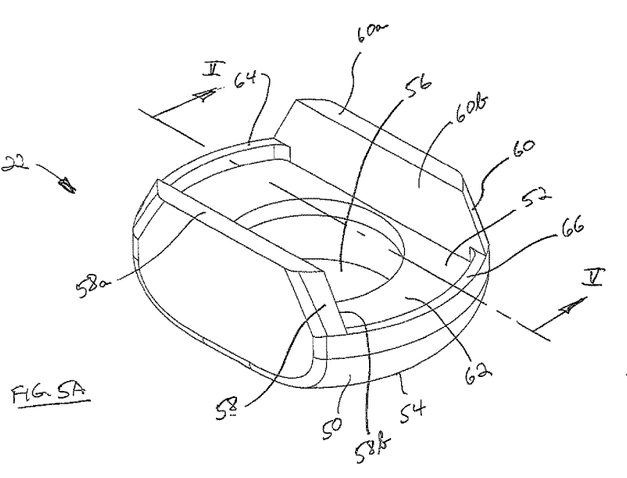
FIG. 5A is a top perspective view of the collar of the translating polyaxial anchor device of FIG. 2.
Figure 5B:
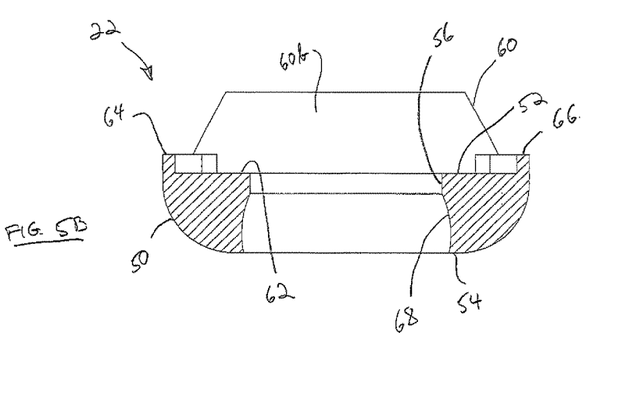
FIG. 5B is a cross-sectional view of the collar as seen along viewing lines V-V of FIG. 5A.
Figure 6:
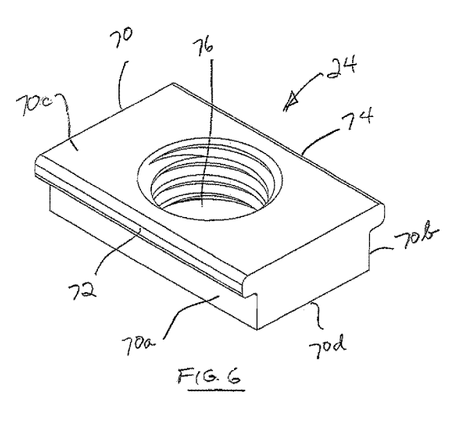
FIG. 6 is a top perspective view of the slider of the translating polyaxial anchor device of FIG. 2.

Referring now to FIGS. 5A, 5B and 6, further the details of the coupling member which comprises collar 22 and slider 24 are described. As shown in FIGS. 5A and 5B, collar 22 comprises a base 50 having an upper surface 52, a lower surface 54 and an opening 56 extending through upper surface 52 and lower surface 54. Upper surface 52 and lower surface 54 are substantially parallel to each other. Base 50 includes a pair of spaced opposing rod supports 58 and 60 projecting upwardly from upper surface 52, rod supports 58 and 60 being that are substantially parallel to each other and that extend along base 50 on either side of opening 56. The upper free ends of each of rod support 58 and 60 terminate in respective rod receiving surfaces 58*a* and 60*a*, rod receiving services 58*a* and 60*a* being generally flat and planar in one particular configuration. Rod receiving surfaces 58*a* and 60*a* are substantially parallel to upper surface 52. Rod supports 58 and 60 include substantially flat inner surfaces 58*b* and 60*b* that define a recess 62 therebetween for receiving yoke 26 and are spaced apart at a dimension for close sliding fit with flat surfaces 46*a* and 46*b* of yoke 26. The floor of recess 62 is defined by upper surface 62. Base 50 further includes a pair of curved opposing spaced lips 64 and 66 extending upwardly from upper surface 52 between rod supports 58 and 60, lips 64 and 66 serving as mechanical stops to limit translating movement of yoke 26 in recess 62, as will be described.

Lower surface 54 of collar 22 includes a cavity 68 having a spherical configuration to substantially match the configuration of the spherical outer surface 30*c* of upper portion 30*b* of the head 30 of bone screw 16. Cavity 68 communicates with opening 56 extending through collar base 50.

As illustrated in FIG. 6, slider 24 comprises a plate 70 that is generally flat and planar. Plate 70 includes a pair of spaced opposing rails 72 and 74 that project outwardly laterally from the side surfaces 70a and 70b of plate 70. Rails 72 and 74 extend along plate 70 generally parallel to each other and define a T-bar configuration for slidable fit with the T-bar slot 48 of yoke 26, as will be described. Slider plate 70 includes an opening 76 extending through the upper surface 70c and the lower surface 70d, opening 76 being internally threaded and configured to threadably receive the external threads on connecting element 20c. Upper surface 70c and lower surface 70d are substantially parallel to each other.

Figure 7:
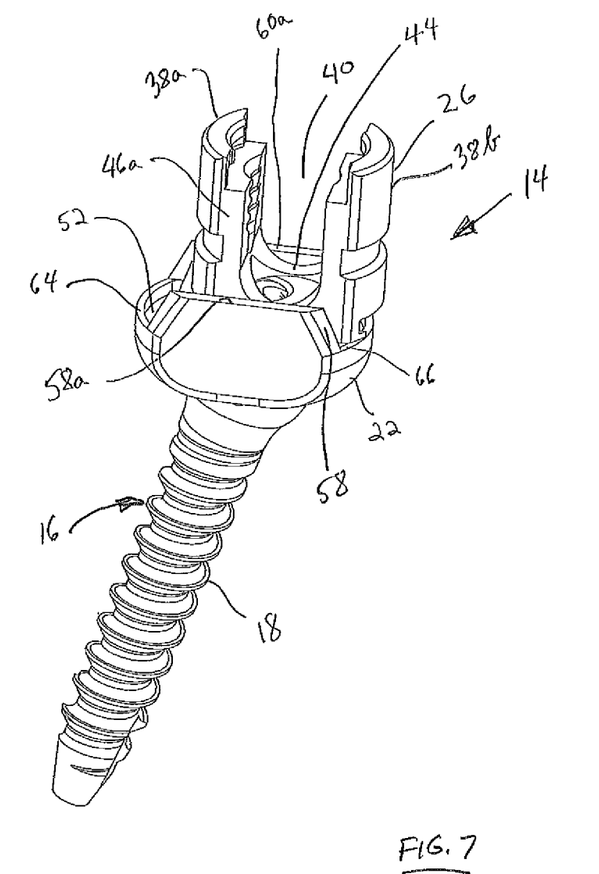
FIG. 7 is a top perspective of the assembled translating polyaxial anchor device of FIG. 2, shown without the set screw fastening element.

Having described the details of the components of the translating polyaxial bone screw 14, the assembly of the components to form the assembled screw 14 as depicted in FIG. 7 is now described. After joining ball insert 20 to head 30 of bone screw 16 as described hereinabove with respect to FIGS. 3A and 3B, collar 22 is placed over bone screw head 30 such that the cavity 68 of lower surface 54 is slidably seated on outer spherical surface 30c of bone screw head 30 with connecting element 20c of ball insert 20 projecting outwardly from head 30 and through collar opening 56. Rails 72 and 74 of slider 24 are slid into T-bar slot 48 until opening 76 of slider 24 is substantially aligned axially with opening 45 through bottom channel surface 44 of yoke 26. The sub-assembly of slider 24 and yoke 26 is placed into collar recess 62 with flat side surfaces 46a and 46b being closely disposed with respect to inner surfaces 58b and 60b of rod supports 58 and 60. A suitable tool (not shown) is attached to ball insert 20 by way of opening 20e for rotating ball insert 20 in a manner to threadably attach the threads of connecting element 20c into the internal threads of slider opening 76 until lower surface 70d of slider plate 70 is seated on upper surface 52 of collar base 50. To further enhance securement, the interface between connecting element 20c and slider 24 at opening 76 may be welded in a conventional manner. At this stage, the translating polyaxial bone screw 14 is fully assembled. As depicted in FIG. 7, upon being assembled, rod receiving surfaces 58a and 60a are situated with respect to yoke 26 such that bottom surface 44 of yoke channel 40 is more proximate upper surface 52 of base 50 of collar 22 than each of receiving surfaces 58a and 60a. Rod receiving surfaces 58a and 60a thus intersect channel 40. Rod receiving surfaces 58a and 60a are disposed substantially perpendicular to axis 20d of connecting element 20c projecting through opening 76 of slider 24. The extent of rod receiving surfaces 58a and 60a between opposed collar lips 64 and 66 is greater than the width of channel 40.

With slider 24 suitably attached to connecting member 20c and supported by collar upper surface 52, collar 22 is slidably retained on spherical outer surface 30c of bone screw 16 such that collar 22 and slider 24 move jointly in polyaxial movement with ball insert 20. Axis 20d of connecting member 20c extends through slider opening 76 such that slider rails 72 and 74 extend generally perpendicular to axis 20d. Yoke 26 which is captured by virtue of the coupling between rails 72 and 74 and yoke T-slot 48 is free to slide transversely relative to axis 20d within collar recess 62, with such transverse sliding being limited by collar lips 64 and 66. Yoke 26 is keyed to collar 26 by virtue of the close sliding fit between yoke flat surfaces 46a and 46b and flat inner surfaces 58b and 60b of rod supports 58 and 60. Thus, yoke 26 is capable of sliding transversely within recess 62 of collar 22 as well as moving polyaxially relative to the bone screw 16.

Figure 9:
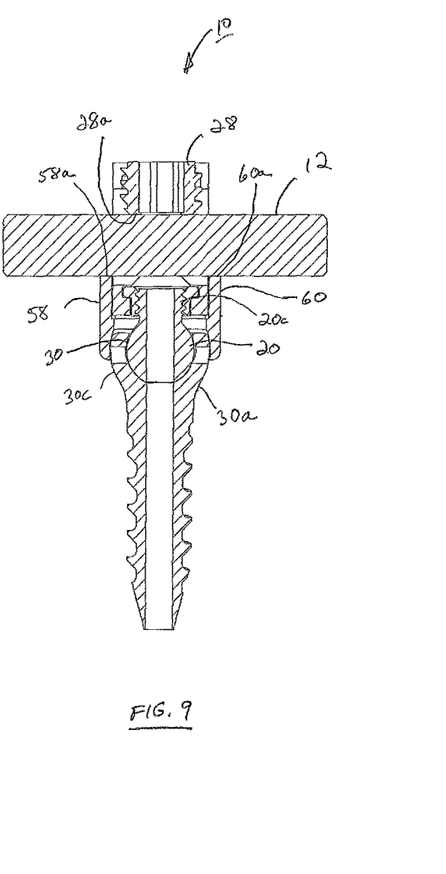
FIG. 9 is a longitudinal cross-sectional view of the spinal fixation system of FIG. 1.

Turning now to FIGS. 8 and 9, the assembly of the connecting rod 12 to translating polyaxial bone screw 14 to form spinal fixation system 10 is shown. Rod 12 is initially placed between the arms 38a and 38b of yoke 26 to rest on the rod receiving surfaces 58a and 60a. Yoke channel 40 may then be closed with fastening element 28 to secure the rod 12 within. Before rod 12 is secured, it should be appreciated that rod 12 may be adjusted longitudinally within channel 40, yoke 26 with rod 12 therein may swivel polyaxially relative to bone screw 16. In addition, yoke 26 may be translated on collar 22 along rod receiving surfaces 58a and 60a. In certain arrangements, yoke 26 may be configured to translate rod 12 approximately 1.5 mm in opposite directions past the center line of the bone screw 16. The combination of polyaxial and translating movement of yoke 26 relative to bone screw 16 allows for proper rod placement in the spine with minimal rod bending.

After the surgeon makes spinal adjustments of rod 12 in the spinal construct, fastening element 28, preferably in the form of a set screw, is provided with external threads to engage the internal threads 42 of yoke arms 38a and 38b. Tightening set screw 28 generates a force that locks ball insert 20 within bone screw 16. More particularly, as set screw 28 is tightened, it presses against rod 12, clamping it between the bottom face 28a of set screw 28 and the rod receiving surfaces 58a and 60a. As set screw 28 is further driven into internal threads 42 of yoke 26, set screw 28 pushes rod 12 downwardly until cavity 68 on lower surface 54 of collar 22 can move no further toward head 30 of the bone screw 16. Any further tightening thereafter results in a reaction force whereby yoke 26 is drawn upwardly. With yoke 26 coupled to slider 24 which in turn is joined to connecting element 20c, upward movement of the yoke pulls slider 24 and ball insert 20 upwardly to forcefully bear the ball 20a against the upper interior spherical surface of socket 32 in bone screw head 30 thereby clamping the wall of socket 32 between collar 22 and ball insert 20. Upward movement of yoke 26 also causes rails 72 and 74 of slider to forcefully engage the surfaces of T-slot 48 at the lower and 26b of yoke 26 to thereby lock yoke 26 relative to slider 24. As such, both polyaxial and translational movement of yoke 26 relative to bone screw 16 are locked upon tightening of set screw 28.

It should now be appreciated that translating polyaxial bone screw 14 allows for suitable placement of screw 14 without compromising rod alignment. Such alignment allows screw 14 to be placed with optimal purchase in the pedicle of a vertebra without the need to over bend rod 12 and to more easily align the channels 40 of adjacent screws 14. By having 1.5 mm translation past the center line of the bone screw 16, rod 12 may also have a straighter trajectory. Rod 12 will thus need less manipulation during insertion with minimal disturbance of the adjacent. In addition the translation of yoke 26 may provide more freedom to use stiffer rods such as those comprising cobalt chrome.

Figure 10:
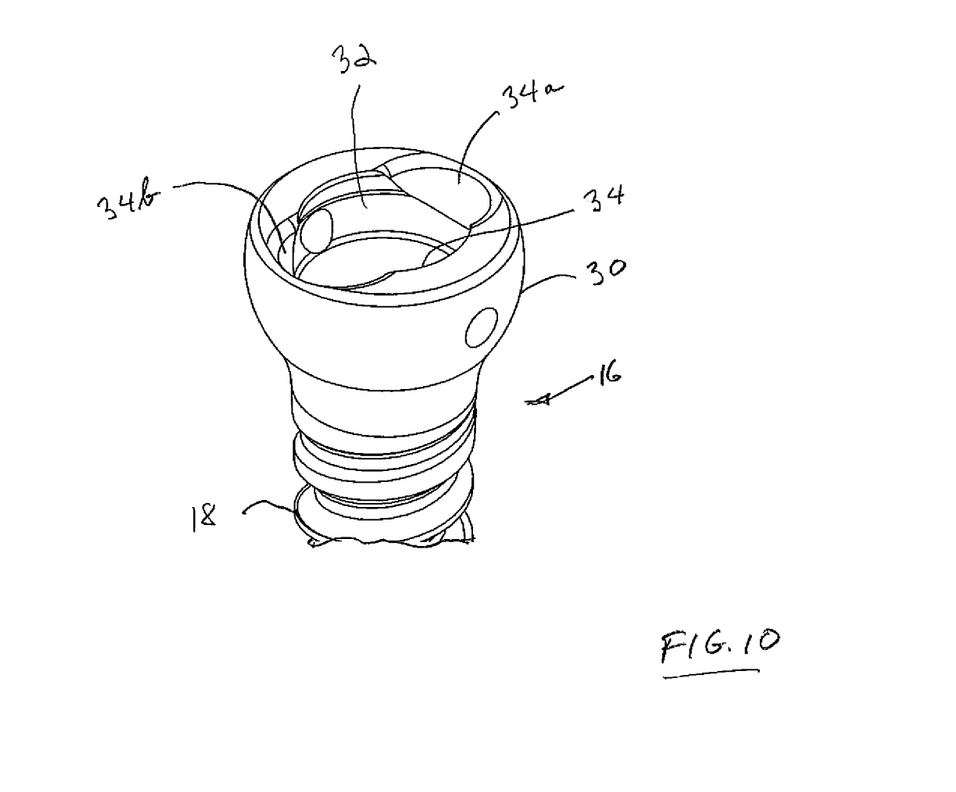
FIG. 10 is a partial top perspective view of the bone screw of FIG. 2 showing a variation of the socket opening for extra angulation of the yoke.

While the invention has been illustrated and described in detail in the drawings and foregoing description, the same should be considered as illustrative and not restrictive in character. One variation is shown, for example in FIG. 10. As illustrated, head 30 of bone screw 16 is formed such that socket opening 34 has two enlarged portions 34a and 34b to provide additional angulation for yoke 26. Enlarged portions 34a and 34b are each sized and configured to angularly receive a thinned neck 20f (FIGS. 3A and 3B) formed between threaded extent of connecting member 20c and the ball of first portion 20a. Receipt of neck 20f in either enlarged portion 34a or 43b allows ball insert 20 and thereby yoke 26 to move angularly an additional amount relative to threaded shank 18 of bone screw 16. In the configuration shown in FIG. 10, such extra angulation is approximately 180 degrees apart. It should be appreciated that socket opening 34 may also be formed to have only one enlarged portion or up to three enlarged portions which would allow extra angulation at approximately 120 degree intervals. In all variations, socket opening 34 with any of the desired enlarged portions is swaged or crimped in a manner to capture ball 20a within socket 32, as described hereinabove. It is therefore understood that only the preferred embodiments have been presented and that all changes, modifications and further applications that come within the spirit of the invention are desired to be protected.

What is claimed is:

1. A translating polyaxial bone anchor assembly for anchoring an elongate connecting rod to a vertebra of a spine, comprising:
    a fastener having a bone engaging portion and a head having an outer surface;
    a yoke having at one end a rod receiving channel defining an axis for receiving an elongate connecting rod and an opposite end including an engagement configuration;
    a coupling assembly coupling said yoke to said fastener in a manner that provides joint polyaxial movement of said yoke relative to said fastener and translational movement of said yoke in a direction transverse to said axis of said channel, said coupling assembly comprising a collar and a slider,
    said collar comprising a base having an upper surface, a lower surface and an opening extending therethrough, said upper surface supporting said slider, said collar having an opening comprising a configuration substantially matching a configuration of, and in sliding engagement with, said outer surface of said head of said fastener, said collar comprising spaced opposing surfaces projecting upwardly from said upper surface of said base and defining a recess therebetween, said yoke engagement configuration being disposed within said collar recess;
    said slider comprising a generally flat plate having an opening extending therethrough, said slider opening being in alignment and communication with said collar opening, said slider being supported within said recess on the upper surface of the base of said collar, said slider including a mateable configuration for cooperative mating with the engagement configuration of said yoke in a manner that slidably couples said yoke with said slider and enables translational movement of said yoke on said slider within said collar recess in a direction transverse to said axis of said channel; and
    a fastening element supported by said yoke for securing said elongate connecting rod in the channel of said yoke between said fastening element and said coupling assembly.

2. The bone anchor assembly of claim 1, wherein said mateable configuration of said slider comprises a pair of spaced laterally projecting rails extending generally parallel to each other.

3. The bone anchor assembly of claim 2, wherein said engagement configuration of said yoke includes a slot configured to slidably engage said pair of slider rails.

4. The bone anchor assembly of claim 3, wherein said pair of slider rails and said yoke slot define a cooperative sliding T-bar/T-slot configuration extending fully across said opposite end of said yoke and transverse to the axis formed by said channel.

5. The bone anchor assembly of claim 4, wherein said coupling assembly includes a mechanical stop to limit translational movement of said yoke within said collar recess.

6. The bone anchor assembly of claim 5, wherein said fastener is a bone screw having a threaded bone engaging shank at one end and said head at an opposite end, said head including an upper portion having said outer surface in the form of a spherical configuration.

7. The bone anchor assembly of claim 6, wherein said opening of said collar comprises a spherical configuration substantially matching the spherical configuration of the outer surface of the head of said fastener.

8. The bone anchor assembly of claim 1, wherein said head includes a socket, an insert captively retained in said socket and configured for swiveling polyaxial movement therein, said insert including an elongate connecting element projecting outwardly from said socket, through said opening of said base and attached to said slider.

* * * * *

UNITED STATES PATENT AND TRADEMARK OFFICE
CERTIFICATE OF CORRECTION

PATENT NO. : 10,278,741 B2
APPLICATION NO. : 15/989309
DATED : May 7, 2019
INVENTOR(S) : Dimitri Protopsaltis et al.

Page 1 of 1

It is certified that error appears in the above-identified patent and that said Letters Patent is hereby corrected as shown below:

In the Specification

At Column 2, Line 51, should read --...invention, reference...--.

At Column 4, Lines 22-23, should read --...perpendicular to an axis formed by channel...--.

Signed and Sealed this
Twenty-fifth Day of June, 2019

Andrei Iancu
*Director of the United States Patent and Trademark Office*